(12) United States Patent
Lyu et al.

(10) Patent No.: US 7,732,065 B2
(45) Date of Patent: Jun. 8, 2010

(54) ANTHRACENE DERIVATIVE COMPOUND AND ORGANIC LIGHT-EMITTING DEVICE INCLUDING THE SAME

(75) Inventors: Yi-yeol Lyu, Yongin-si (KR); Eun-sil Han, Yongsin-si (KR); Young-hun Byun, Yongin-si (KR); Myeong-suk Kim, Suwon-si (KR); Dong-woo Shin, Seoul (KR); Byoung-ki Choi, Hwaseong-si (KR); O-hyun Kwon, Seoul (KR); Woon-jung Paek, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 319 days.

(21) Appl. No.: 11/833,722

(22) Filed: Aug. 3, 2007

(65) Prior Publication Data

US 2008/0111478 A1 May 15, 2008

(30) Foreign Application Priority Data

Nov. 10, 2006 (KR) .................. 10-2006-0111237

(51) Int. Cl.
*C09K 11/06* (2006.01)
(52) U.S. Cl. .................... 428/690; 544/35; 427/56
(58) Field of Classification Search .............. None
See application file for complete search history.

(56) References Cited

U.S. PATENT DOCUMENTS

| 4,356,429 A | 10/1982 | Tang |
| 4,885,211 A | 12/1989 | Tang et al. |
| 5,151,629 A | 9/1992 | Vanslyke |

FOREIGN PATENT DOCUMENTS

| JP | 1999003782 | | 1/1999 |
| JP | 2004-002351 | * | 1/2004 |
| JP | 2005-170809 | * | 6/2005 |

OTHER PUBLICATIONS

English Translation of JP 2004-002351 (undated).*

(Continued)

*Primary Examiner*—D. Lawrence Tarazano
*Assistant Examiner*—Gregory Clark
(74) *Attorney, Agent, or Firm*—Cantor Colburn LLP

(57) ABSTRACT

Provided are an anthracene derivative compound represented by Formula 1 below and an organic light-emitting device using the same:

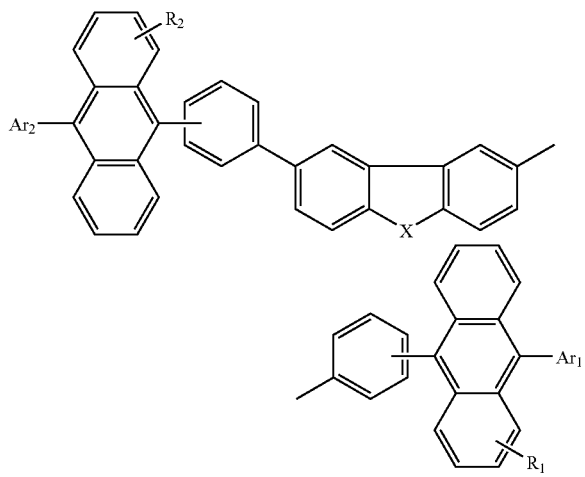

wherein
$Ar_1$ and $Ar_2$ are each independently aromatic groups, $R_1$ and $R_2$ are each independently substituent groups, and X is a heteroatom or substituted heteroatom. The use of the anthracene derivative compound enables to produce an organic light-emitting device with better driving voltage, brightness, efficiency, and color purity.

16 Claims, 2 Drawing Sheets

| SECOND ELECTRODE | 170 |
| ELECTRON INJECTION LAYER | 160 |
| ELECTRON TRANSPORT LAYER | 150 |
| EMITTING LAYER | |
| HOLE TRANSPORT LAYER | 140 |
| HOLE INJECTION LAYER | 130 |
| FIRST ELECTRODE | 120 |
| | 110 |

| SECOND ELECTRODE | 170 |
| ELECTRON INJECTION LAYER | 160 |
| ELECTRON TRANSPORT LAYER | 150 |
| EMITTING LAYER | |
| HOLE INJECTION LAYER | 140 |
| FIRST ELECTRODE | 120 |
| | 110 |

OTHER PUBLICATIONS

Kuwabara, et al.; "Thermally Stable Multilayered Organic Electroluminescent Devices Using Novel Starburst Molecules, 4,4',4"-Tri(N-carbazolyl)triphenylamine (TCTA) and 4,4'4"-Tris(3-methylphenylphenyl-amino)triphenylamine (m-MTDATA), as Hole-Transport Materials"; Adv. Mater.; vol. 6, No. 9; pp. 677-679; 1994.

"Organic Electroluminescence, Zakya H. Kafafi, ed., CRC press, Taylor & Francis Group pp. 168-172 (2005)".

* cited by examiner

FIG. 1C

| SECOND ELECTRODE | 170 |
| --- | --- |
| ELECTRON INJECTION LAYER | 160 |
| ELECTRON TRANSPORT LAYER | 150 |
| HOLD BLOCKING LAYER | 180 |
| EMITTING LAYER | 140 |
| HOLE TRANSPORT LAYER | 130 |
| HOLE INJECTION LAYER | 120 |
| FIRST ELECTRODE | 110 |

# ANTHRACENE DERIVATIVE COMPOUND AND ORGANIC LIGHT-EMITTING DEVICE INCLUDING THE SAME

This application claims priority to Korean Patent Application No. 10-2006-0111237, filed on Nov. 10, 2006, and all the benefits accruing therefrom under 35 U.S.C. §119(a), the disclosure of which is incorporated herein by reference in its entirety.

BACKGROUND OF THE INVENTION

1. Field of the Invention

The present invention relates to an anthracene derivative compound and an organic light-emitting device including the same. More particularly, the present invention relates to an anthracene derivative compound that has good electrical characteristics, and when applied to an organic light-emitting device, can offer excellent driving voltage, efficiency, and color purity characteristics, and an organic light-emitting device employing an organic layer including the anthracene derivative compound.

2. Description of the Related Art

Organic light-emitting devices are active emission display devices that emit light by recombination of electrons and holes in a thin layer (hereinafter, referred to as "organic layer") formed of a fluorescent or phosphorescent organic compound when a current is supplied to the organic layer. The organic light-emitting devices have advantages such as lightness, simple constitutional elements, easy fabrication process, superior image quality, and wide viewing angle. In addition, the organic light-emitting devices can perfectly create dynamic images, achieve high color purity, and have electrical properties suitable for portable electronic equipment due to low power consumption and low driving voltage.

Eastman Kodak Co. has developed an organic light-emitting device with a multi-layered structure including an aluminum quinolinol complex layer and a triphenylamine derivative layer (U.S. Pat. No. 4,885,211), and an organic light-emitting device including an organic light-emitting layer formed of a low molecular weight material capable of emitting light in a broad wavelength range from UV to infrared light (U.S. Pat. No. 5,151,629).

Light-emitting devices are self-emitting devices and have advantages such as a wide viewing angle, good contrast, and a rapid response time. Light-emitting devices are classified into inorganic light-emitting devices using an emitting layer formed of an inorganic compound and Organic Light-Emitting Devices ("OLEDs") using an emitting layer formed of an organic compound. OLEDs show better brightness, driving voltage, and response speed characteristics and can create polychromatic light, compared to inorganic light-emitting devices, and thus, extensive research into OLEDs has been conducted.

Generally, OLEDs have a stacked (i.e., layered) structure having in sequence an anode, an organic light-emitting layer, and a cathode. OLEDs may also have various, more specific structures such as anode/hole injection layer/hole transport layer/emitting layer/electron transport layer/electron injection layer/cathode structure or an anode/hole injection layer/hole transport layer/emitting layer/hole blocking layer/electron transport layer/electron injection layer/cathode structure.

Materials used for OLEDs can be classified generally as either vacuum-depositable materials and solution-coatable materials according to an organic layer formation process. Vacuum-depositable materials must have a vapor pressure of $10^{-6}$ torr or more at 500° C. or less, and may be low molecular weight materials having a molecular weight of 1,200 g/mol or less. Solution-coatable materials must have solubility sufficient to form solutions, and can include those materials incorporating an aromatic or heterocyclic ring.

When manufacturing OLEDs using a vacuum deposition process, manufacturing costs may increase due to use of a vacuum system, and it may be difficult to manufacture high-resolution pixels for natural color displays using a shadow mask. On the other hand, when manufacturing OLEDs using a solution coating process, such as, for example inkjet printing, screen printing, or spin coating, the manufacturing process is simple, manufacturing costs are low, and a relatively high resolution can be achieved for the pixels when compared to those prepared using a shadow mask.

However, when using solution-coatable materials, the performance (e.g., thermal stability, color purity) of light-emitting molecules is lowered compared to when using vacuum-depositable materials. Even though the light-emitting molecules of the solution-coatable materials have good performance, there arise problems that the materials, when formed into an organic layer, gradually crystallize and grow into a size that is comparable to visible light wavelength range, and thus, such crystals scatter visible light, thereby causing an observable turbidity phenomenon, and pinholes, and other defects, may be formed in the organic layer, thereby causing device degradation.

Japanese Patent Laid-Open Publication No. 1999-003782 discloses a 2-naphthyl-substituted anthracene compound that can be used in an emitting layer or a hole injection layer. However, OLEDs employing the anthracene compound are unsatisfactory in terms of driving voltage, brightness, efficiency, and color purity characteristics, and thus, there is room for improvement in conventional OLEDs.

BRIEF SUMMARY OF THE INVENTION

The present invention provides an anthracene derivative compound capable of improving the driving voltage, efficiency, and color purity characteristics of an organic light-emitting device, and an organic light-emitting device including the same.

According to an embodiment, there is provided an anthracene derivative compound represented by Formula 1 below:

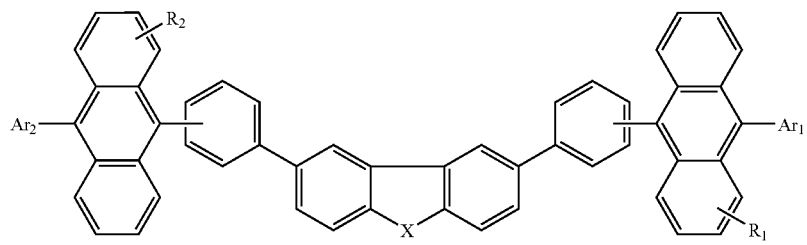

Formula 1 wherein, $Ar_1$ and $Ar_2$ are each independently selected from the group consisting of a substituted or unsubstituted $C_5$~$C_{20}$ aryl group, a substituted or unsubstituted $C_1$~$C_{20}$ cycloaryl group, and a substituted or unsubstituted $C_6$~$C_{20}$ arylalkyl group;

$R_1$ and $R_2$ are each independently selected from the group consisting of hydrogen, halogen, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{20}$ heterocycloalkyl group, a substituted or unsubstituted $C_1$~$C_{20}$ alkoxy group, a substituted or unsubstituted $C_6$~$C_{20}$ aryl group, a substituted or unsubstituted $C_6$~$C_{20}$ arylalkyl group, and a substituted or unsubstituted $C_2$~$C_{20}$ heteroaryl group; and X is O, S, or NR' where R' is a substituted or unsubstituted $C_1$~$C_{20}$ alkyl group, a substituted or unsubstituted $C_3$~$C_{20}$ cycloalkyl group, a substituted or unsubstituted $C_1$~$C_{20}$ alkoxy group, a substituted or unsubstituted $C_6$~$C_{30}$ aryl group, or a substituted or unsubstituted $C_6$~$C_{30}$ aralkyl group.

The anthracene derivative compound may be represented by Formula 2 below:

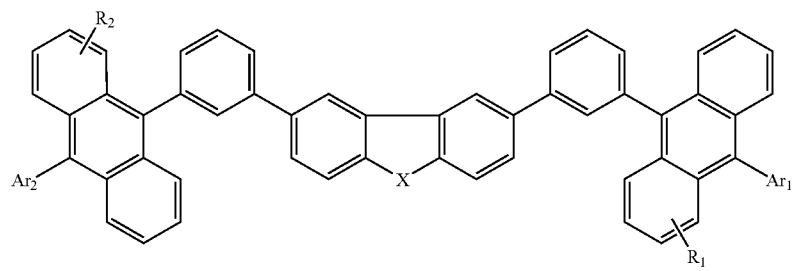

Formula 2 wherein, $Ar_1$ and $Ar_2$ are each independently selected from the group consisting of a substituted or unsubstituted $C_5$~$C_{20}$ aryl group, a substituted or unsubstituted $C_1$~$C_{20}$ cycloaryl group, and a substituted or unsubstituted $C_6$~$C_{20}$ arylalkyl group;

$R_1$ and $R_2$ are each independently selected from the group consisting of hydrogen, halogen, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{20}$ heterocycloalkyl group, a substituted or unsubstituted $C_1$~$C_{20}$ alkoxy group, a substituted or unsubstituted $C_6$~$C_{20}$ aryl group, a substituted or unsubstituted $C_6$~$C_{20}$ arylalkyl group, and a substituted or unsubstituted $C_2$~$C_{20}$ heteroaryl group; and X is O, S, or NR' where R' is a substituted or unsubstituted $C_1$~$C_{20}$ alkyl group, a substituted or unsubstituted $C_3$~$C_{20}$ cycloalkyl group, a substituted or unsubstituted $C_1$~$C_{20}$ alkoxy group, a substituted or unsubstituted $C_6$~$C_{30}$ aryl group, or a substituted or unsubstituted $C_6$~$C_{30}$ aralkyl group.

According to another embodiment, there is provided an organic light-emitting device including: a first electrode; a second electrode; and at least one organic layer interposed between opposing surfaces of the first electrode and the second electrode, the organic layer including the above-described anthracene derivative compound.

In another embodiment, a method of manufacturing an organic light-emitting device comprises forming a first electrode; forming an organic layer comprising an anthracene derivative compound of Formulas 1 or 2 on a surface of the first electrode; and forming a second electrode on a surface of the organic layer opposite the first electrode.

The organic light-emitting device including the anthracene derivative compound can show better driving voltage, efficiency, and color purity.

BRIEF DESCRIPTION OF THE DRAWINGS

The above and other features and advantages of the present invention will become more apparent by describing in detail exemplary embodiments thereof with reference to the attached drawings in which:

FIGS. 1A through 1C are schematic views illustrating organic light-emitting devices according to embodiments of the present invention.

DETAILED DESCRIPTION OF THE INVENTION

Figure 1A:
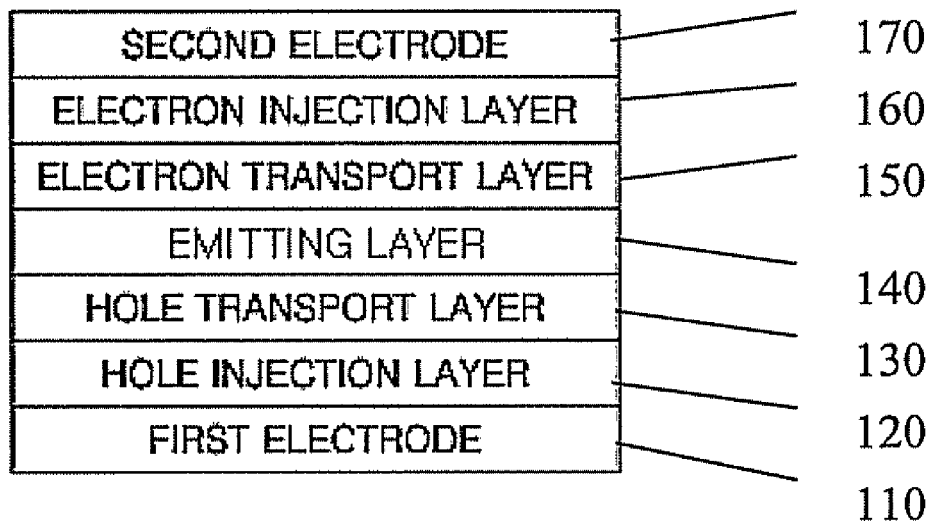

The present invention will now be described more fully with reference to the accompanying drawings, in which exemplary embodiments of the invention are shown.

It will be understood that when an element is referred to as being "on" another element, it can be directly on the other element or intervening elements may be present therebetween. In contrast, when an element is referred to as being "disposed on", "interposed between", or "formed on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As disclosed herein, an anthracene derivative compound is represented by Formula 1 below:

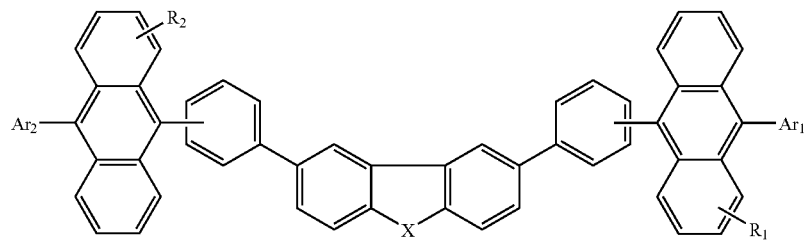

Formula 1 wherein, $Ar_1$ and $Ar_2$ are each independently aromatic groups selected from the group consisting of a substituted or unsubstituted $C_5$~$C_{20}$ aryl group, a substituted or unsubstituted $C_1$~$C_{20}$ cycloaryl group, and a substituted or unsubstituted $C_6$~$C_{20}$ arylalkyl group;

$R_1$ and $R_2$ are each independently substituent groups selected from the group consisting of hydrogen, halogen, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{20}$ heterocycloalkyl group, a substituted or unsubstituted $C_1$~$C_{20}$ alkoxy group, a substituted or unsubstituted $C_6$~$C_{20}$ aryl group, a substituted or unsubstituted $C_6$~$C_{20}$ arylalkyl group, and a substituted or unsubstituted $C_2$~$C_{20}$ heteroaryl group; and X is a heteroatom or substituted heteroatom selected from O, S, or NR' where R' is a substituted or unsubstituted $C_1$~$C_{20}$ alkyl group, a substituted or unsubstituted $C_3$~$C_{20}$ cycloalkyl group, a substituted or unsubstituted $C_1$~$C_{20}$ alkoxy group, a substituted or unsubstituted $C_6$~$C_{30}$ aryl group, or a substituted or unsubstituted $C_6$~$C_{30}$ aralkyl group.

Preferably, the phenylene moieties of the anthracene derivative compound of Formula 1 may be incorporated to form the meta-positions of the phenylene moieties. That is, the anthracene derivative compound of Formula 1 may be a compound represented by Formula 2 below:

substituted or unsubstituted $C_3$~$C_{20}$ cycloalkyl group, a substituted or unsubstituted $C_5$~$C_{20}$ heterocycloalkyl group, a substituted or unsubstituted $C_1$~$C_{20}$ alkoxy group, a substituted or unsubstituted $C_6$~$C_{20}$ aryl group, a substituted or unsubstituted $C_6$~$C_{20}$ arylalkyl group, and a substituted or unsubstituted $C_2$~$C_{20}$ heteroaryl group; and X is O, S, or NR' where R' is a substituted or unsubstituted $C_1$~$C_{20}$ alkyl group, a substituted or unsubstituted $C_3$~$C_{20}$ cycloalkyl group, a substituted or unsubstituted $C_1$~$C_{20}$ alkoxy group, a substituted or unsubstituted $C_6$~$C_{30}$ aryl group, or a substituted or unsubstituted $C_6$~$C_{30}$ aralkyl group.

Examples of the unsubstituted alkyl group as used herein include methyl, ethyl, propyl, isobutyl, sec-butyl, tert-butyl, pentyl, iso-amyl, and hexyl. At least one hydrogen atom of the alkyl group may be substituted by a halogen atom, a hydroxy group, a nitro group, a cyano group, a substituted or unsubstituted amino group (—$NH_2$, —NH(R), —N(R')(R'') where R' and R'' are each independently a $C_1$-$C_{10}$ alkyl group), an amidino group, hydrazine, hydrazone, a carboxyl group, a sulfonyl group, a phosphonyl group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The aryl group as used herein refers to a carbocyclic aromatic system containing one or more aromatic rings. The rings may be attached to each other as a pendant group or may be fused. For example, the aryl group may be an aromatic group such as phenyl, naphthyl, or tetrahydronaphthyl. At

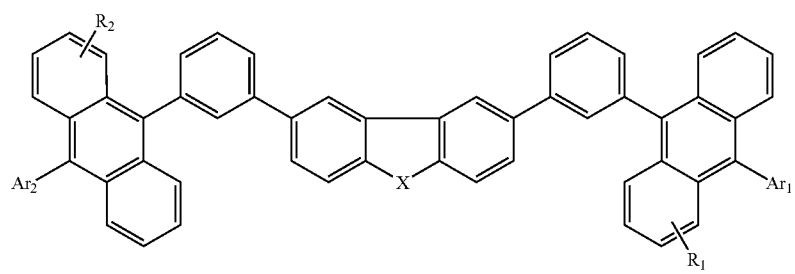

Formula 2 wherein, $Ar_1$ and $Ar_2$ are each independently selected from the group consisting of a substituted or unsubstituted $C_5$~$C_{20}$ aryl group, a substituted or unsubstituted $C_1$~$C_{20}$ cycloaryl group, and a substituted or unsubstituted $C_6$~$C_{20}$ arylalkyl group;

$R_1$ and $R_2$ are each independently selected from the group consisting of hydrogen, halogen, cyano group, a hydroxyl group, a substituted or unsubstituted $C_1$~$C_{20}$ alkyl group, a least one hydrogen atom of the aryl group may be substituted by the same substituents as those mentioned in the above definition of the alkyl group.

The term "substituted" as used herein to define substituent(s) refers to the replacement of a hydrogen atom with a substituent. Examples of the substituent include a $C_1$-$C_{12}$ alkyl group, a $C_1$-$C_{12}$ alkoxy group, a halogen atom such as fluorine or chlorine, a $C_1$-$C_{30}$ lower alkylamino group, a hydroxy group, a nitro group, a cyano group, a substituted or unsubstituted amino group (—NH$_2$, —NH(R), —N(R')(R'') where R' and R'' are each independently a C$_1$-C$_{12}$ alkyl group), a carboxyl group, a sulfonyl group, a phosphonyl group, a C$_1$-C$_{20}$ halogenated alkyl group, an alkenyl group, an alkynyl group, a heteroalkyl group, a C$_6$-C$_{30}$ aryl group, an arylalkyl group, a heteroaryl group, and a C$_2$-C$_{30}$ heteroarylalkyl group.

According to an exemplary embodiment, the anthracene derivative compound may be selected from compounds represented by Formulae 3 through 8 below, but is not limited thereto:

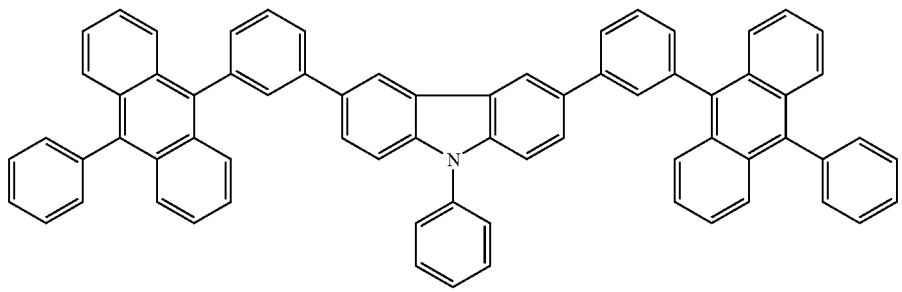

Formula 3

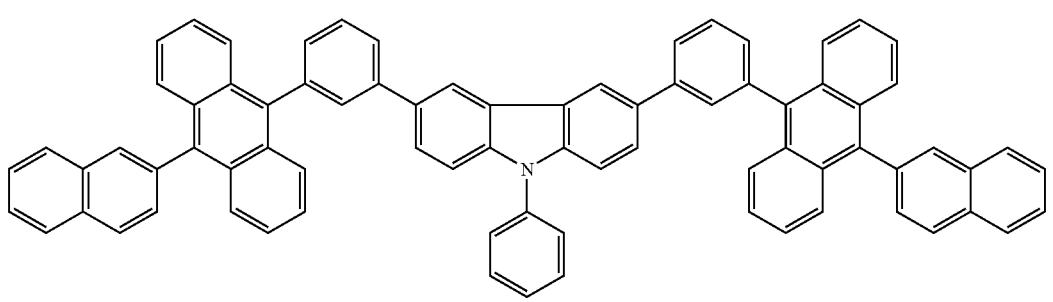

Formula 4

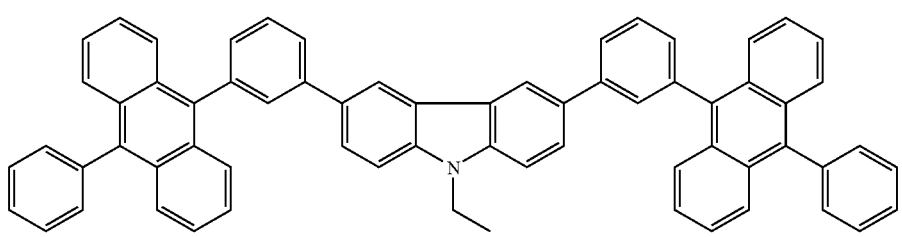

Formula 5

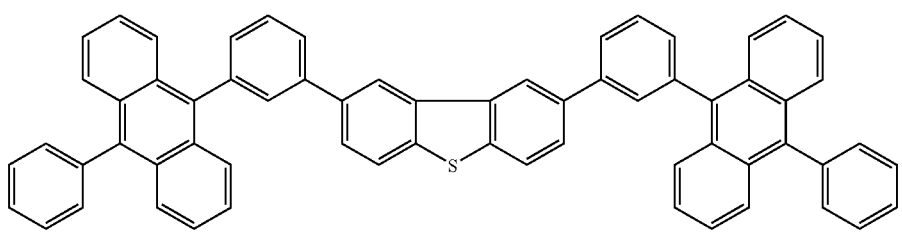

Formula 6

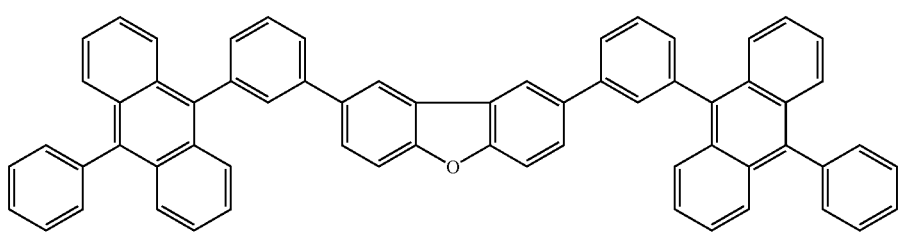

Formula 7

-continued

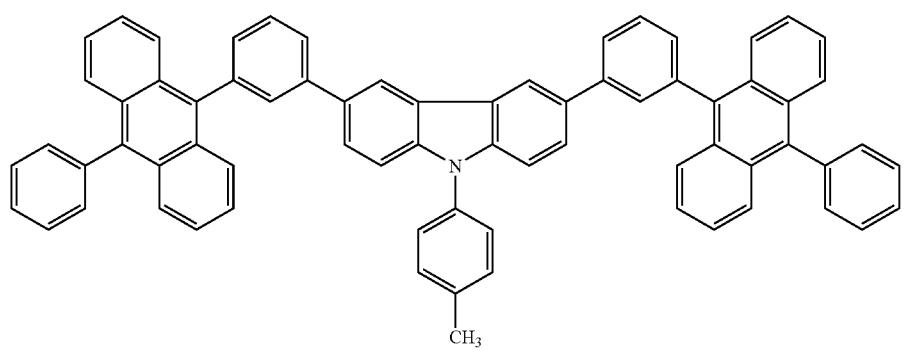

Formula 8

Compounds represented by Formula 1 can be synthesized using a conventional synthesis method. Detailed synthesis procedures for these compounds are exemplified by the reaction schemes provided in the following synthesis examples.

Also provided herein is an organic light-emitting device including: a first electrode; a second electrode; and at least one organic layer interposed between opposing surfaces of the first electrode and the second electrode, where the organic layer includes an anthracene derivative compound represented by Formula 1.

Specifically, in the organic light-emitting device, the compound of Formula 1 may be a compound represented by Formula 2 above. More specifically, in the organic light-emitting device, the compound of Formula 1 may be a compound selected from compounds represented by Formulae 3 through 8 above.

The anthracene derivative compounds disclosed herein are suitable to be used as a host for the organic layer, in particular for an emitting layer, where the organic layer has blue light-emitting characteristics.

The emitting layer may further include another emitting material, in addition to the anthracene derivative compounds disclosed herein.

The organic light-emitting device can be variously structured. At least one selected from the group consisting of a hole injection layer, a hole transport layer, a hole blocking layer, an electron blocking layer, an electron transport layer, and an electron injection layer may be further interposed between opposing surfaces of the first electrode and the second electrode.

Figure 1B:
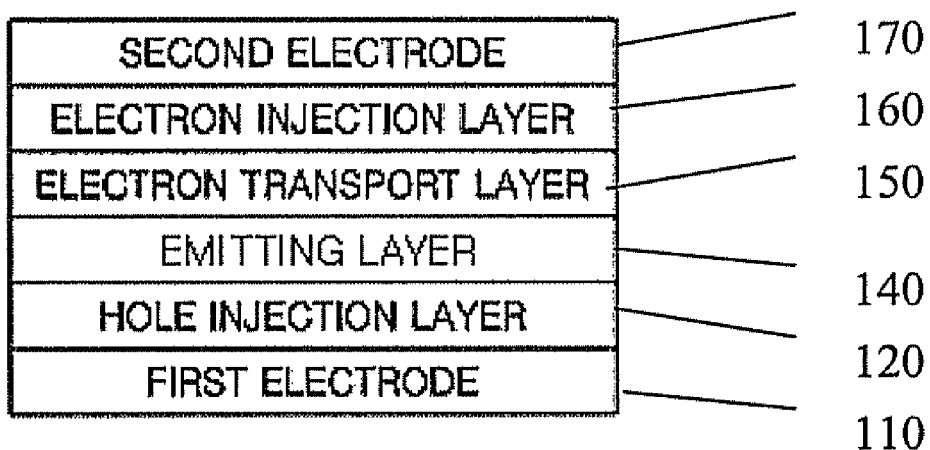

In more detail, organic light-emitting devices according to exemplary embodiments are illustrated in FIGS. 1A, 1B, and 1C. Referring to FIG. 1A, an organic light-emitting device has a stacked (i.e., layered) structure comprising a first electrode 110/hole injection layer 120/hole transport layer 130/emitting layer 140/electron transport layer 150/electron injection layer 160/second electrode 170. Referring to FIG. 1B, an organic light-emitting device has a stacked structure comprising a first electrode 110/hole injection layer 120/emitting layer 140/electron transport layer 150/electron injection layer 160/second electrode 170. Referring to FIG. 1C, an organic light-emitting device has a stacked structure comprising a first electrode 110/hole injection layer 120/hole transport layer 130/emitting layer 140/hole blocking layer 180/electron transport layer 150/electron injection layer 160/second electrode 170. Here, at least one of the emitting layer 140, the hole injection layer 120, and the hole transport layer 130 may include an anthracene derivative compound according to an embodiment.

An emitting layer 140 of the organic light-emitting device may include a red, green, blue, or white phosphorescent or fluorescent dopant. The phosphorescent dopant may be an organometallic compound including at least one element selected from the group consisting of Ir, Pt, Os, Ti, Zr, Hf, Eu, Tb, and Tm.

In general, the organic light emitting device as disclosed herein can be manufactured by a method comprising forming a first electrode; forming an organic layer comprising an anthracene derivative compound of Formulas 1 or 2 on a surface of the first electrode; and forming a second electrode on a surface of the organic layer opposite the first electrode. In an embodiment, an organic light emitting device is prepared according to this method.

Hereinafter, a more detailed method of manufacturing an organic light-emitting device will be described with reference to FIG. 1C.

First, a first electrode material with a high work function is formed on a surface of a substrate (not shown) using deposition or sputtering to form a first electrode 110. The first electrode 110 may be an anode. Here, the substrate may be a substrate commonly used in organic light-emitting devices. Specifically, the substrate may be a glass or transparent plastic substrate having high mechanical strength, thermal stability, transparency, surface smoothness, handling properties, and water repellency. The first electrode material can be a material with transparency and good conductivity, such as for example, indium tin oxide ("ITO"), indium zinc oxide ("IZO"), tin oxide ($SnO_2$), or zinc oxide (ZnO).

Next, a hole injection layer ("HIL") 120 may be formed on a surface of the first electrode 110 opposite the substrate using various methods such as vacuum deposition, spin-coating, casting, or Langmuir-Blodgett (LB) method.

Where forming of the hole injection layer 120 is done using a vacuum deposition process, the deposition conditions will vary according to the type of hole injection layer material, the structure and thermal characteristics of the hole injection layer 120, and the like. However, it is desirable that the hole injection layer 120 should be deposited to a thickness of about 10 Å to about 5 μm at a deposition rate of about 0.01 to about 100 Å/sec, at a temperature of 100 to 500° C., in a vacuum level of $10^{-8}$ to $10^{-3}$ torr.

Where forming of the hole injection layer 120 is done using a spin-coating process, the coating conditions will vary according to the type of hole injection layer material, the structure and thermal characteristics of the hole injection layer, and the like. However, it is desirable that the spin-coating be performed at a coating speed of about 2,000 to 5,000 rpm, and, after the spin-coating, a thermal treatment be performed at a temperature of about 80 to 200° C. for the purpose of solvent removal.

The hole injection layer material may be a compound of Formula 1 or 2 as described above. In addition, the hole injection layer material may be a known hole injection material, such as a phthalocyanine compound, for example copper phthalocyanine, as disclosed in U.S. Pat. No. 4,356,429; a Starburst-type amine derivative such as, for example, 4,4',4"-tris(N-carbazolyl)-triphenylamine ("TCTA"), 4,4',4"-tris(3-methylphenylphenylamino)triphenylamine ("m-MTDATA"), or 1,3,4-tris{4-[methylphenyl(phenyl)amino]phenyl}benzene ("m-MTDAPB") as disclosed in *Advanced Materials,* 1994, vol. 6, p. 677;, or a soluble conductive polymer, such as, for example, polyaniline/dodecylbenzenesulfonic acid ("Pani/DBSA"), poly(3,4-ethylenedioxythiophene)/poly(4-styrenesulfonate) ("PEDOT/PSS"), polyaniline/camphor sulfonic acid ("Pani/CSA"), or polyaniline/poly(4-styrenesulfonate) ("PANI/PSS").

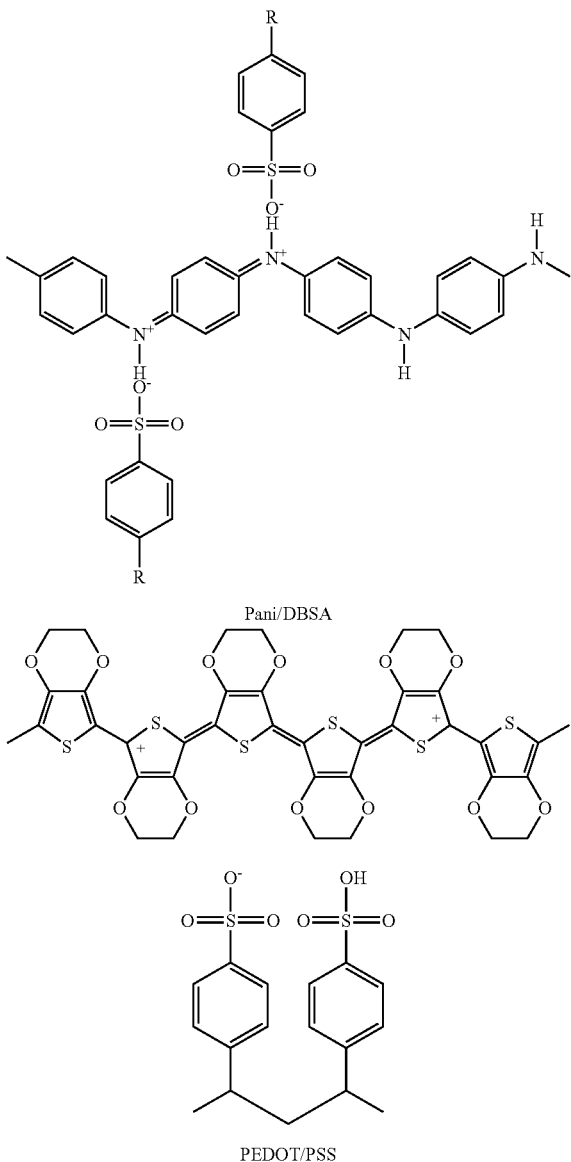

The hole injection layer 120 may be formed to a thickness of about 100 to about 10,000 Å, specifically about 100 to about 1,000 Å. If the thickness of the hole injection layer is less than about 100 Å, hole injection characteristics may be lowered. On the other hand, if the thickness of the hole injection layer is greater than about 10,000 Å, the driving voltage may increase.

Next, a hole transport layer ("HTL") 130 may be formed on a surface of the hole injection layer 120 opposite first electrode 110 using various methods such as vacuum deposition, spin-coating, casting, or LB method. Where forming the hole transport layer is done using vacuum deposition or spin-coating, the deposition or coating conditions will vary according to the type of compound used, but are generally comparable to those used for the formation of the hole injection layer 120.

A hole transport layer material may be a compound of Formula 1 as described above. In addition, the hole transport layer material can be a known hole transport material, such as for example a carbazole derivative such as N-phenylcarbazole or polyvinylcarbazole; an amine derivative having an aromatic fused ring such as N,N'-bis(3-methylphenyl)-N,N'-diphenyl-[1,1-biphenyl]-4,4'-diamine ("TPD") or N,N'-di(naphthalene-1-yl)-N,N'-diphenylbenzidine ("α-NPD"); or the like.

The hole transport layer 130 may be formed to a thickness of about 50 to about 1,000 Å, specifically about 100 to about 600 Å. If the thickness of the hole transport layer 130 is less than about 50 Å, hole transport characteristics may be reduced. On the other hand, if the thickness of the hole transport layer is greater than about 1,000 Å, the driving voltage may increase.

Next, an emitting layer ("EML") 140 may be formed on a surface of the hole transport layer 130 opposite hole injection layer 120 using vacuum deposition, spin-coating, casting, or LB method. Where forming of the emitting layer is done using vacuum deposition or spin-coating, the deposition or coating conditions will vary according to the type of compound used, but are generally comparable to those used for the formation of the hole injection layer 120.

The emitting layer 140 may include an anthracene derivative compound of Formula 1 as described above. Here, a known host or dopant material suitable for use with the compound of Formula 1 may also be included. The anthracene derivative compound of Formula 1 may be used as a phosphorescent host alone or in combination with 4,4'-N,N'-dicarbazole-biphenyl ("CBP"), poly(n-vinylcarbazole ("PVK"), and the like. A phosphorescent dopant, may be used including a red phosphorescent dopant such as platinum octatethyl porphine ("PtOEP", available as RD 61 from UDC), a green phosphorescent dopant such as Ir(PPy)$_3$ (where PPy=2-phenylpyridine), or a blue phosphorescent dopant such as iridium (III) bis[4,6-di-fluorophenyl)-pyridinato-N,C$^{2'}$]picolinate ("F$_2$Irpic").

When the anthracene derivative compound of Formula 1 is used as a single host, the doping concentration of a dopant is not particularly limited. Generally, the content of the dopant is 0.01 to 15 parts by weight, based on 100 parts by weight of the host. On the other hand, when the anthracene derivative compound of Formula 1 is used as a host in combination with another host, the content of the compound of Formula 1 is 30 to 99 parts by weight based on the total weight (100 parts by weight) of the hosts.

The emitting layer 140 may be formed to a thickness of about 100 to about 1,000 Å, specifically about 200 to about 600 Å. If the thickness of the emitting layer is less than about 100 Å, emission characteristics may be reduced. On the other hand, if the thickness of the emitting layer is greater than about 1,000 Å, the driving voltage may increase.

Where the emitting layer 140 includes a phosphorescent dopant, the hole blocking layer ("HBL") 180 may be formed on the hole transport layer 130 using vacuum deposition, spin-coating, casting, or LB method, in order to prevent the diffusion of triplet excitons or holes into the electron transport layer 150. Where forming of the hole blocking layer 180 is done using vacuum deposition or spin coating, the deposition or coating conditions will vary according to the type compound used, but are generally comparable to those used for the formation of the hole injection layer 120. An available hole blocking material may be an oxadiazole derivative, a triazole derivative, a phenanthroline derivative such as 2,9-dimethyl-4,7-diphenyl-1,10-phenanthroline ("BCP"), an aluminum complex, and the like.

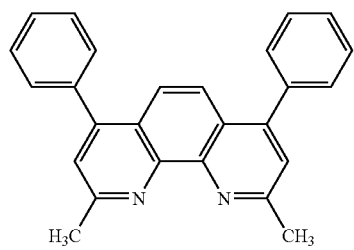
Phenanthroline-containing organic compound

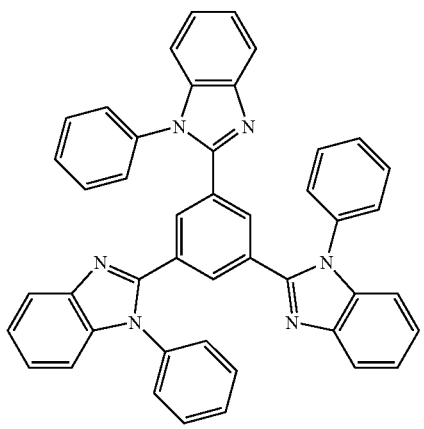
Imidazole-containing organic compound

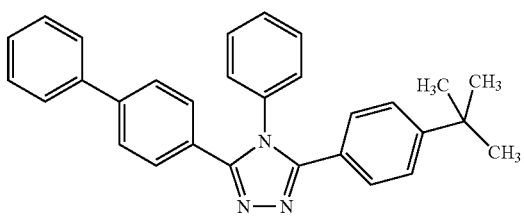
Triazole-containing organic compound

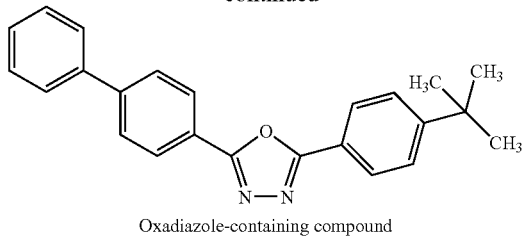
Oxadiazole-containing compound

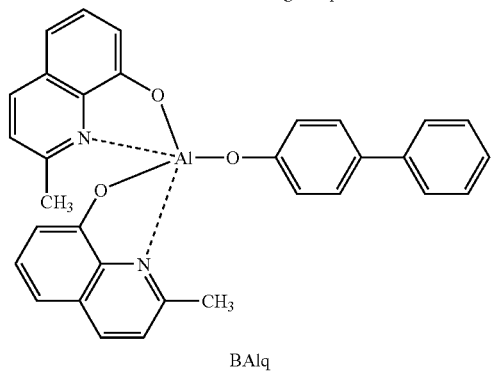
BAlq

The hole blocking layer 180 may be formed to a thickness of about 50 to about 1,000 Å, specifically about 100 to about 300 Å. If the thickness of the hole blocking layer 180 is less than about 50 Å, hole blocking characteristics may be reduced. On the other hand, if the thickness of the hole blocking layer 180 is greater than about 1,000 Å, the driving voltage may be increase.

Next, an electron transport layer ("ETL") 150 may be formed using various methods such as vacuum deposition, spin-coating, or casting. Where forming of the electron transport layer 150 is done using vacuum deposition or spin-coating, the deposition or coating conditions will vary according to the type of compound used, but are generally comparable to those used for forming of the hole injection layer 120. An electron transport layer material serves to transport electrons from an electron donor electrode (a cathode) and may be a known material such as an oxazole-based compound, an isoxazole-based compound, a triazole-based compound, an isothiazole-based compound, an oxadiazole-based compound, a thiadiazole-based compound, a perylene-based compound, an aluminum complex (such as, for example, tris(8-quinolinolato)-aluminum ("Alq3"), bis(2-methyl-8-quinolinolato)-aluminum biphenolate ("Balq"), bis(2-methyl-8-quinolinolato)-aluminum triphenylsilicide ("SAlq"), or tris(2-methyl-8-quinolinolato)-aluminum ("Almq3"); a gallium complex such as for example bis(2-methyl-8-quinolinolato)-gallium pivalate ("Gaq'2OPiv"), bis(2-methyl-8-quinolinolato)-gallium acetate ("Gaq'2OAc"), μ-oxo-bis[bis (2-methyl-8-quinolinolato)-gallium] ("2(Gaq'2)"), and the like.

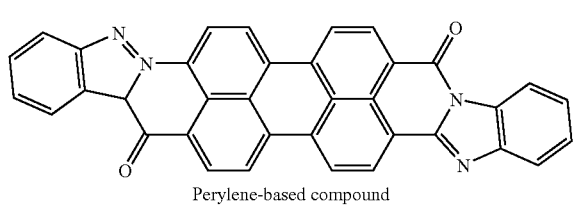
Perylene-based compound

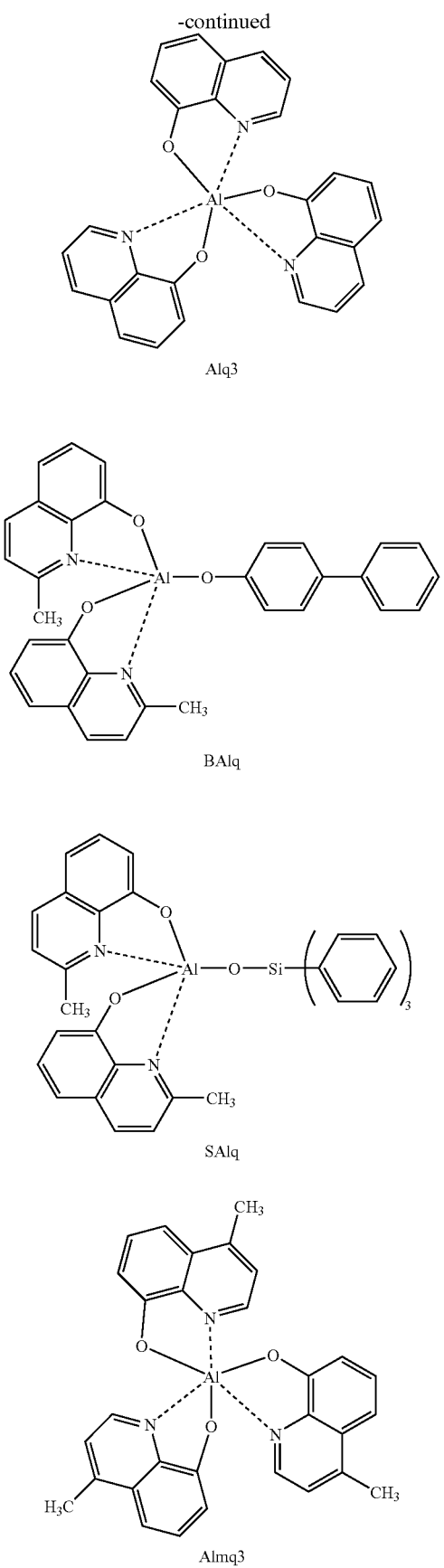
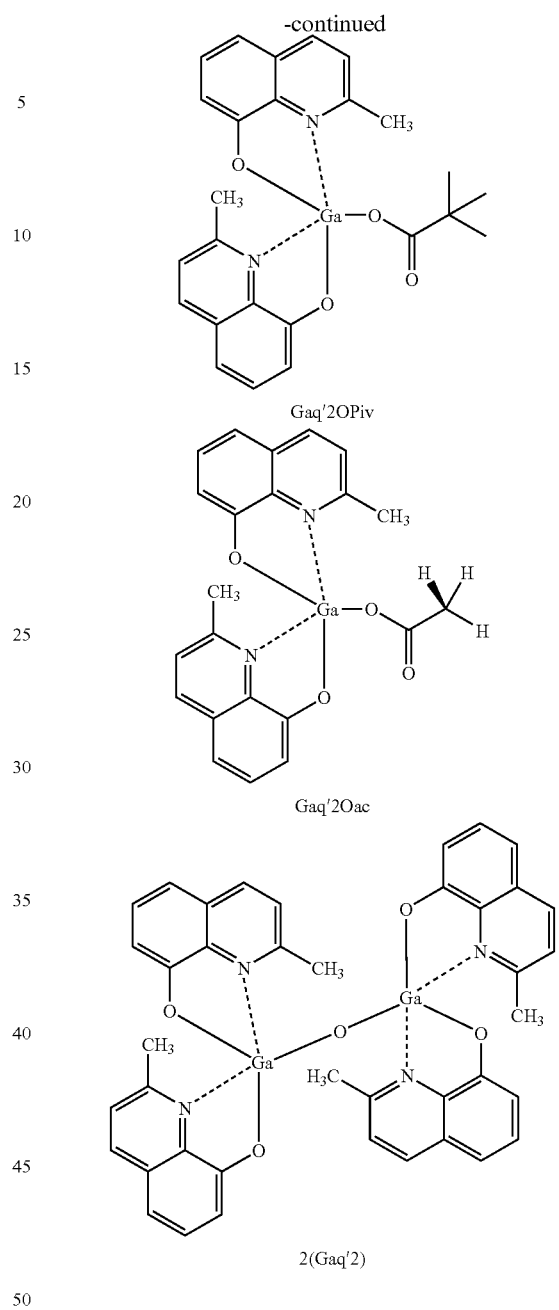

The electron transport layer 150 may be formed to a thickness of about 100 to about 1,000 Å, specifically about 200 to about 500 Å. If the thickness of the electron transport layer 150 is less than about 100 Å, electron transport characteristics may be reduced. On the other hand, if the thickness of the electron transport layer 150 is greater than about 1,000 Å, the driving voltage may increase.

An electron injection layer ("EIL") 160 may be formed on a surface of the electron transport layer 150 opposite hole blocking layer 180 in order to facilitate the injection of electrons from a cathode into the electron injection layer 160. An electron injection layer material is not particularly limited.

The electron injection layer material may be selected from known materials such as for example LiF, NaCl, CsF, $Li_2O$, or BaO. The deposition conditions of the electron injection layer vary according to the type of a used compound, but are generally almost the same as those for the formation of the hole injection layer 120.

The electron injection layer 160 may be formed to a thickness of about 1 to about 100 Å, specifically about 5 to about 50 Å. If the thickness of the electron injection layer 160 is less than about 1 Å, electron injection characteristics may be reduced. On the other hand, if the thickness of the electron injection layer is greater than about 100 Å, the driving voltage may increase.

Finally, a second electrode 170 may be formed on a surface of the electron injection layer 160 opposite electron transport layer 150 using vacuum deposition or sputtering. The second electrode 170 may be used as a cathode. A material for forming the second electrode 170 may be metal or alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), etc. The second electrode 170 may also be a transmissive cathode formed of ITO or IZO to provide a front-emission type device.

Hereinafter, the present invention will be described more specifically with reference to the following working examples. However, the following examples are only for illustrative purposes and are not intended to limit the scope of the invention.

Synthesis Example 1

Synthesis of Intermediate A

An intermediate A was synthesized according to Reaction Scheme 1 below:

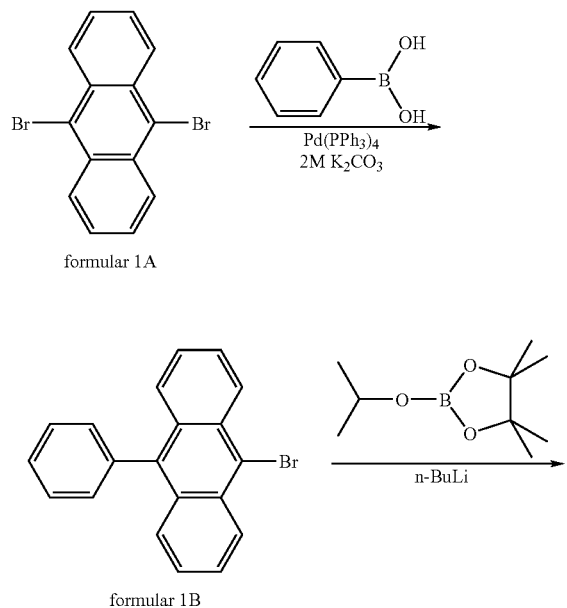

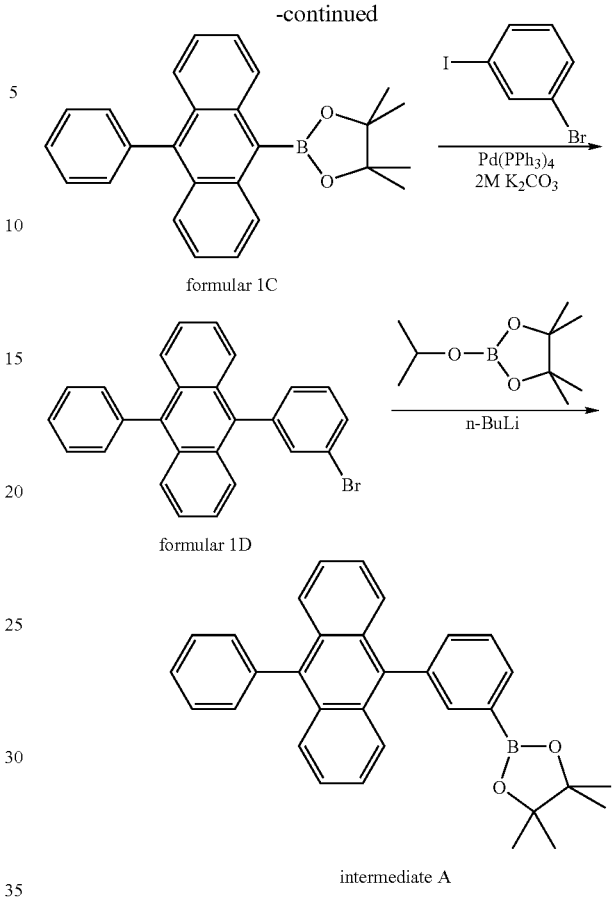

9,10-dibromoanthracene (4.00 g, 11.90 mmol) and phenylboronic acid (1.60 g, 13.12 mmol) were dissolved in toluene (100 ml), and Pd(PPh$_3$)$_4$ (0.68 g, 0.59 mmol) and 2M K$_2$CO$_3$ (24 ml) were gradually dropwise added thereto. The reaction mixture was refluxed for 48 hours and cooled to room temperature. Then, a solvent was removed under a reduced pressure, and the residue was extracted with chloroform. The extracted solution was twice washed with a supersaturated sodium chloride solution and water (H$_2$O), and an organic layer was collected and dried over anhydrous magnesium sulfate. Then, the solvent was evaporated to obtain a crude product, and the crude product was purified by silica gel column chromatography using as an eluant, a solution of chloroform and hexane (1:1 v/v) to give 2.27 g (yield: 57%) of a compound of Formula 1b. The compound of Formula 1b (2.20 g, 6.60 mmol) was dissolved in tetrahydrofuran (100 ml), and n-butyllithium (4.6 ml, 7.36 mmol, 1.6 M solution) and 2-isopropoxy-4,4,5,5-tetramethyl-1,3,2-dioxaborolane (1.48 ml, 7.25 mmol) were gradually dropwise added thereto at −78° C. The reaction mixture was gradually heated to room temperature and incubated at room temperature for 15 hours. Then, water (H$_2$O) (50 ml) was added to the reaction solution so that the reaction was terminated, and the resultant solution was extracted with chloroform. The extracted solution was twice washed with a supersaturated sodium chloride solution and water (H$_2$O), and an organic layer was collected and dried over anhydrous magnesium sulfate. Then, the solvent was evaporated to obtain a crude product, and the crude product was purified by silica gel column chromatography using as an eluant, a solution of chloroform and hexane (1:1 v/v) to give 1.53 g (yield: 61%) of a compound of Formula 1c. A compound of Formula 1d (1.80 g, yield: 61%) was synthesized in the same manner as in the synthesis of the compound of Formula 1b except that 3-bromoiodobenzene was used instead of 9,10-dibromoanthracene, and the compound of Formula 1c (2.75 g, 7.23 mmol) was used instead of phenylboronic acid. The intermediate A (1.70 g, yield: 56%) was synthesized in the same manner as in the synthesis of the compound of Formula 1c except that the compound of Formula 1d (2.70 g, 6.60 mmol) was used instead of the compound of Formula 1b.

Synthesis Example 2

Synthesis of Compound of Formula 3

A compound of Formula 3 was synthesized in the same manner as in the synthesis of the compound of Formula 1b except that 3,6-dibromo-9-phenylcarbazole was used instead of 9,10-dibromoanthracene, and the intermediate A was used instead of phenylboronic acid.

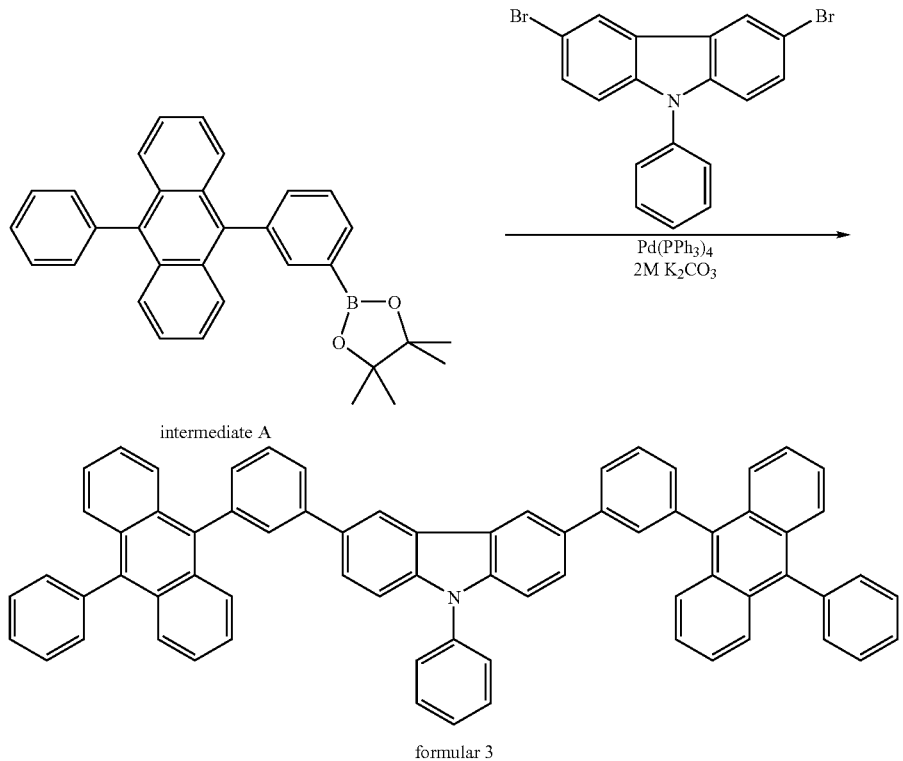

Synthesis Example 3

Synthesis of Compound of Formula 5

A compound of Formula 5 was synthesized in the same manner as in the synthesis of the compound of Formula 1b except that 3,6-dibromo-9-ethylcarbazole was used instead of 9,10-dibromoanthracene, and the intermediate A was used instead of phenylboronic acid.

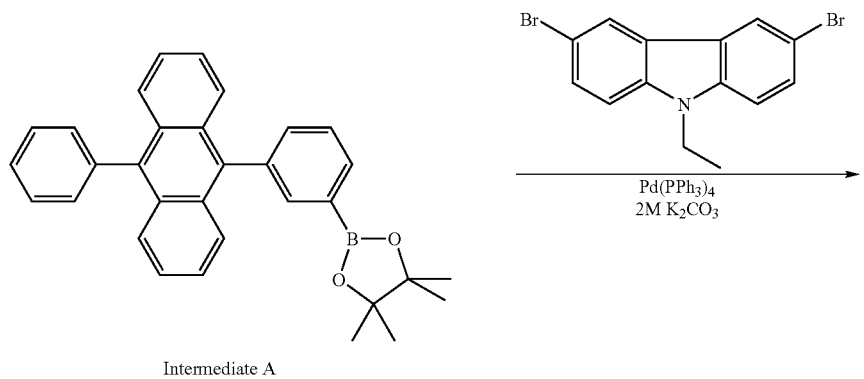

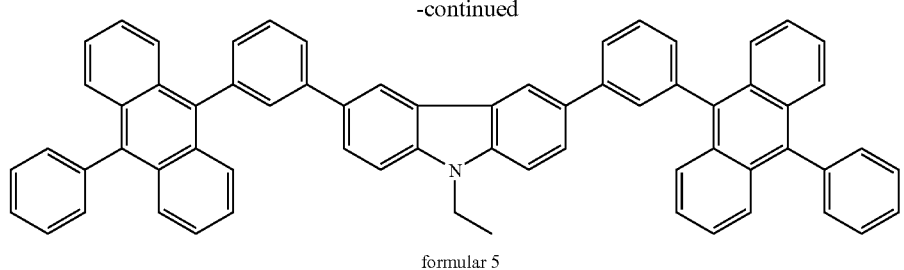
formular 5
Synthesis Example 4
Synthesis of Compound of Formula 6
A compound of Formula 6 was synthesized in the same manner as in the synthesis of the compound of Formula 1b except that 2,8-dibromodibenzothiophene was used instead of 9,10-dibromoanthracene, and the intermediate A was used instead of phenylboronic acid.
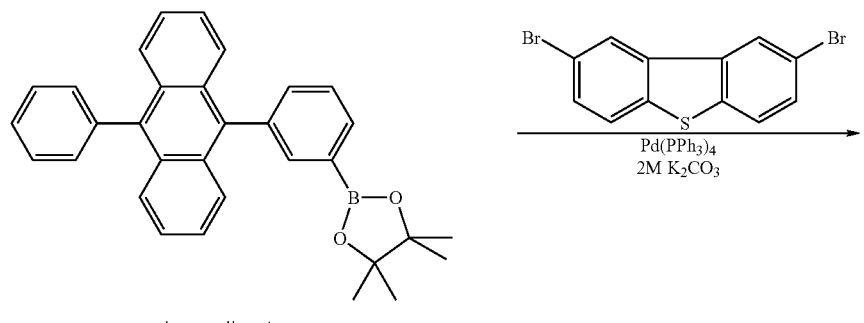
Reaction Scheme 4
intermediate A
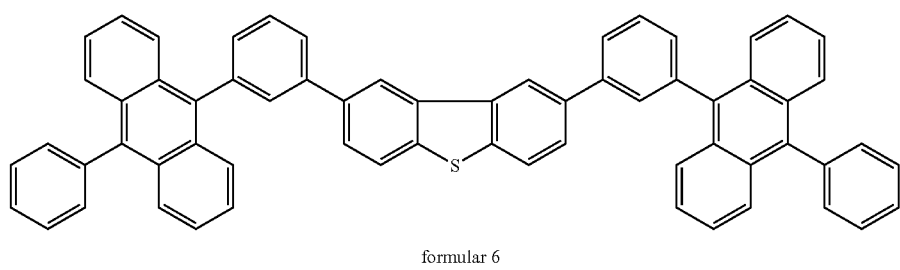
formular 6

That is, the compound of Formula 6 was synthesized according to Reaction Scheme 2 except that the intermediate A reacted with 3,6-dibromodibenzothiophene, instead of 3,6-dibromo-9-phenylcarbazole.

Synthesis Example 5

Synthesis of Compound of Formula 7

A compound of Formula 7 was synthesized in the same manner as in the synthesis of the compound of Formula 1b except that 2,8-dibromodibenzofuran was used instead of 9,10-dibromoanthracene, and the intermediate A was used instead of phenylboronic acid.

Reaction Scheme 5

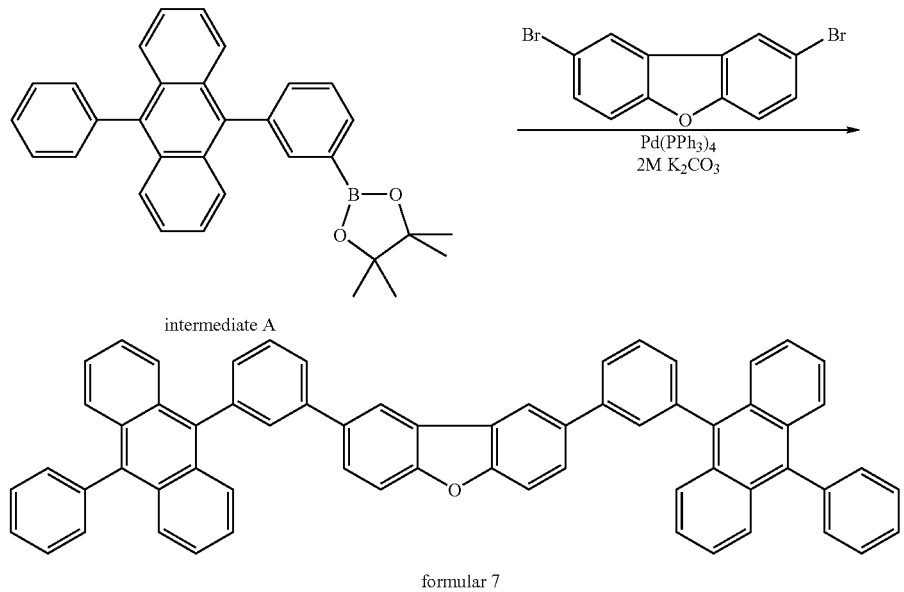

Synthesis Example 6

Synthesis of Compound of Formula 8

A compound of Formula 8 was synthesized in the same manner as in the synthesis of the compound of Formula 1b except that 3,6-dibromo-9-tolylcarbazole was used instead of 9,10-dibromoanthracene, and the intermediate A was used instead of phenylboronic acid.

Reaction Scheme 6

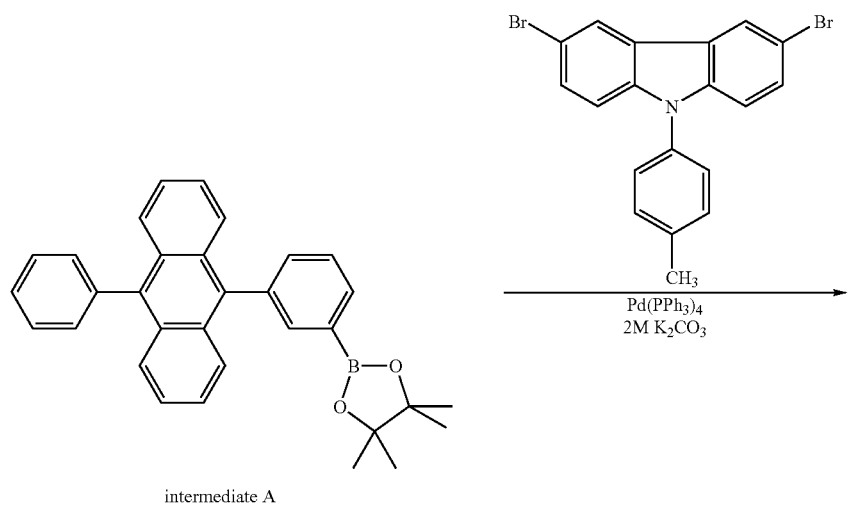

-continued
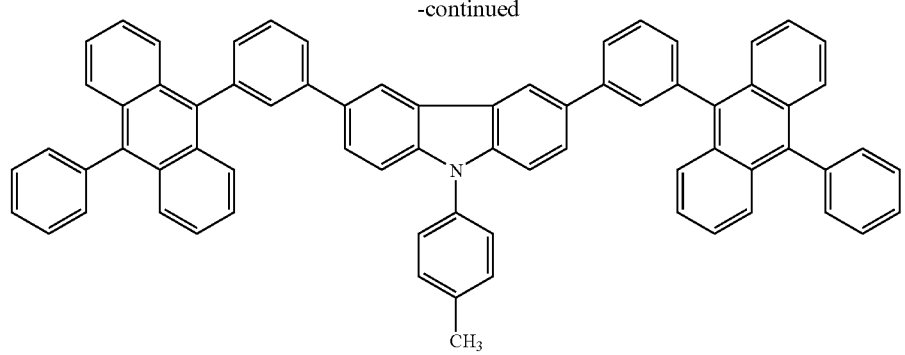
formular 8
Synthesis Example 7
Synthesis of Compound of Formula 4
An intermediate B
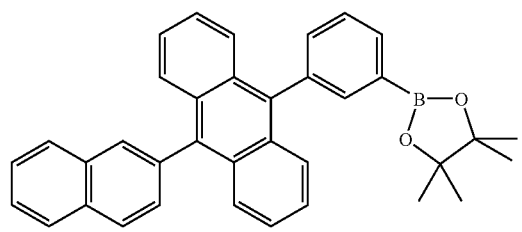
was synthesized in the same manner as in Synthesis Example 1 except that
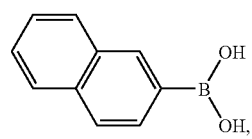
instead of
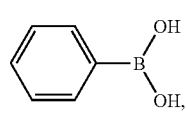
reacted with the compound of Formula 1a.
Reaction Scheme 7
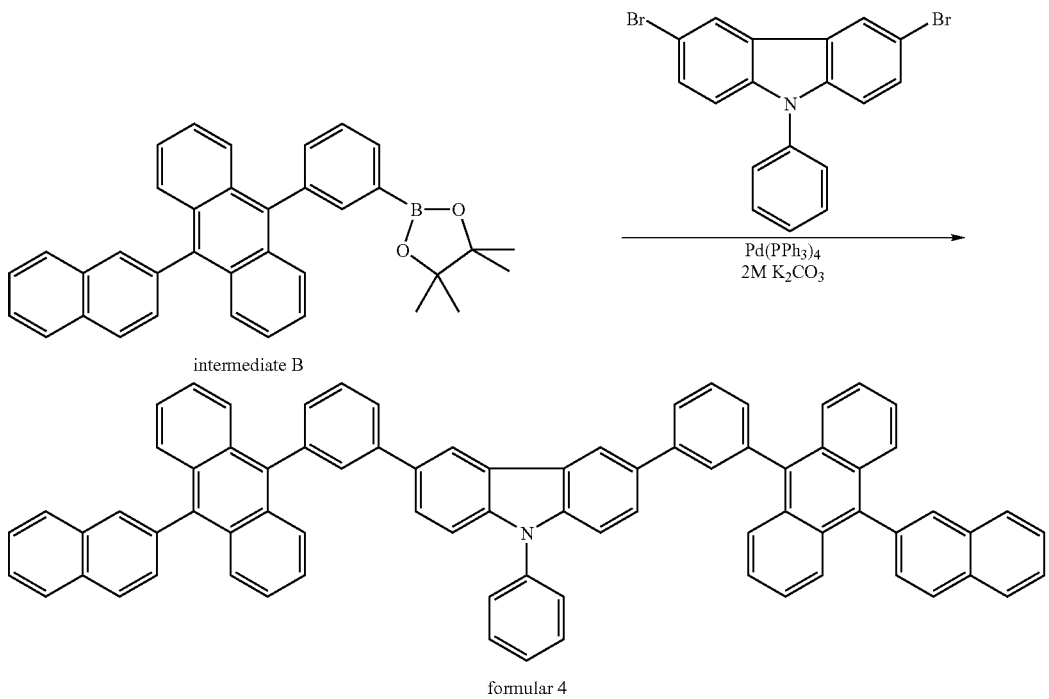
intermediate B
formular 4

A compound of Formula 4 was synthesized from the intermediate B according to Reaction Scheme 7. That is, the compound of Formula 4 was synthesized according to Reaction Scheme 2 except that the intermediate B was used instead of the intermediate A.

The compounds of Formulae 3 through 8 were identified by $^1$H NMR spectroscopy and LC-Mass spectrometry.

Evaluation Example 1

Evaluation of Emission Characteristics

The photoluminescence (PL) spectra of the compounds of Formulae 3-8 in a solution phase and a film phase were measured to evaluate the emission characteristics of the compounds of Formulae 3-8.

In order to evaluate optical characteristics of a solution phase, the compound of Formula 3 was diluted with toluene to a concentration of 10 mM, and the PL spectrum of the diluted solution was measured using an ISC PC1 spectrofluorometer equipped with a xenon lamp. The same experiment was performed for the compounds of Formulae 4-8. The results are presented in Table 1 below.

On the other hand, in order to evaluate optical characteristics of a film phase, quartz substrates were prepared and washed with acetone and pure water. Then, the compound of Formula 3 was spin-coated on the substrates and heated at 110° C. for 30 minutes to form films with a thickness of about 1,000 Å. The PL spectra of the films were measured. The same experiment was performed for the compounds of Formulae 4-8. The results are presented in Table 2 below.

TABLE 1

| Compound | Maximum absorption wavelength (nm) | Maximum PL wavelength (nm) |
|---|---|---|
| Formula 3 | 357, 376, 397 | 412, 432 |
| Formula 4 | 357, 378, 397 | 420, 440 |
| Formula 5 | 357, 376, 397 | 412, 432 |
| Formula 6 | 356, 375, 396 | 411, 431 |
| Formula 7 | 356, 375, 396 | 410, 431 |
| Formula 8 | 357, 376, 397 | 412, 432 |

TABLE 2

| Compound | Maximum absorption wavelength (nm) | Maximum PL wavelength (nm) |
|---|---|---|
| Formula 3 | 361, 380, 401 | 422, 442 |
| Formula 4 | 361, 381, 401 | 432, 452 |
| Formula 5 | 361, 380, 401 | 422, 441 |
| Formula 6 | 360, 379, 400 | 420, 440 |
| Formula 7 | 362, 379, 400 | 421, 442 |
| Formula 8 | 361, 380, 401 | 423, 444 |

The results of Tables 1 and 2 show that the anthracene derivative compounds of Formulas 3-8, have emission characteristics that are suitable for used in an organic light-emitting device.

Example 1

Organic light-emitting devices having the following structure were manufactured using each compound of Formulae 3-8 as a host of an emitting layer and DPAVBi as a dopant for the emitting layer: ITO (1,000 Å)/M-TDATA (35 nm)/α-NPD (30 nm)/(each compound of Formulae 3-8=95 wt %/DPAVBi=5 wt %) (35 nm)/ALq3 (18 nm)/LiF (0.7 nm)/Al (150 nm). The structure of DPAVBi was as follows.

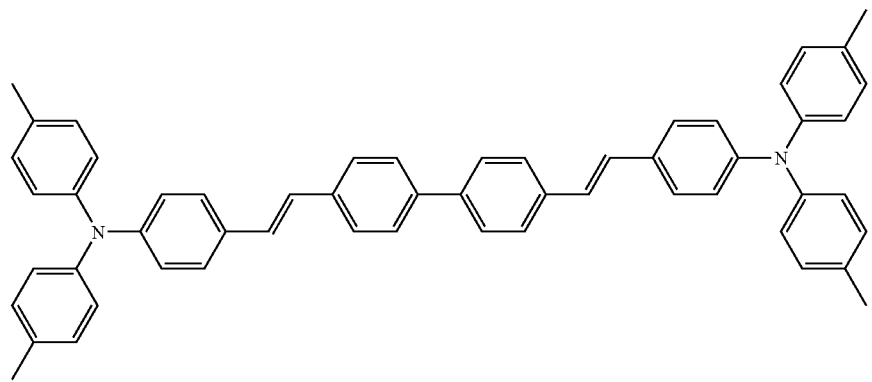

DPAVBi

A 15 Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. M-TDATA was spin-coated to a thickness of 35 nm on the anodes and α-NPD was then spin-coated thereon to a thickness of 30 nm. Then, a solution of each compound of Formulae 3-8 and DPAVBi (weight ratio (wt %) of 95:5) in toluene was spin-coated to a thickness of 35 nm to form emitting layers. Then, ALq3 was vacuum-deposited to a thickness of 18 nm on the emitting layers to form electron transport layers. LiF (0.7 nm, electron injection layers) and Al (150 nm, cathodes) were sequentially vacuum-deposited on the electron transport layers to thereby complete organic light-emitting devices as illustrated in FIG. 1B. The emission characteristics of the devices are summarized in Table 3 below.

Comparative Example 1

Organic light-emitting devices were manufactured in the same manner as in Example 1 except that DPAVBi only was used as a light-emitting material, without using an anthracene derivative compound according to the present invention. The emission characteristics of the devices are summarized in Table 3 below. The results for maximum current efficiency are reported in units of candles per ampere (cd/A), and the results for CIE luminance are reported in units of candles per square meter (cd/m²).

TABLE 3

| Compound | Driving voltage (V) | Maximum current efficiency (cd/A) | External quantum efficiency (%) | CIE coordinate (~100 cd/m²) |
|---|---|---|---|---|
| DPAVBi | 4.5 | 2.10 | 0.9 | (0.15, 0.23) |
| Formula 3 | 3.8 | 6.66 | 4.2 | (0.15, 0.21) |
| Formula 4 | 3.7 | 6.81 | 4.3 | (0.15, 0.20) |
| Formula 5 | 3.6 | 6.72 | 4.2 | (0.15, 0.20) |
| Formula 6 | 3.4 | 7.12 | 4.5 | (0.15, 0.20) |
| Formula 7 | 3.5 | 7.02 | 4.3 | (0.15, 0.21) |
| Formula 8 | 3.8 | 6.57 | 4.2 | (0.15, 0.21) |

From the above Examples, it can be seen that an anthracene derivative compound according to the present invention which constitutes an emitting layer of an organic light-emitting device has good emission characteristics as a phosphorescent or fluorescent material.

An anthracene derivative compound of Formula 1 according to the present invention has excellent emission characteristics. Therefore, the use of the anthracene derivative compound of Formula 1 of the present invention enables to produce an organic light-emitting device having a low driving voltage, good color purity, high efficiency, and high external quantum efficiency.

What is claimed is:

1. An anthracene derivative compound represented by Formula 2 below:

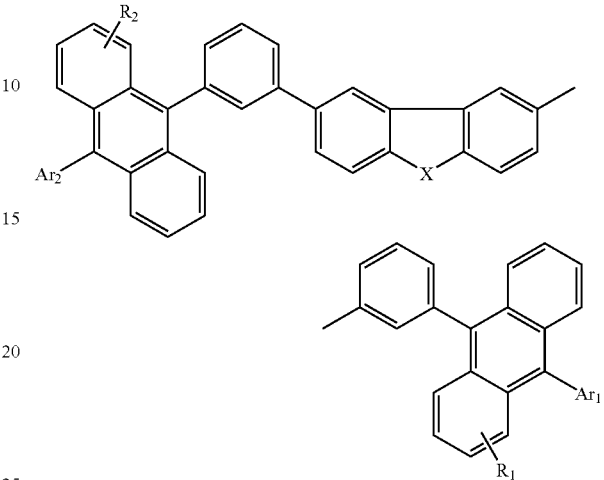

Formula 2 wherein

Ar₁ and Ar₂ are each independently selected from the group consisting of a substituted or unsubstituted $C_5$~$C_{20}$ aryl group, a substituted or unsubstituted $C_1$~$C_{20}$ cycloaryl group, and a substituted or unsubstituted $C_6$~$C_{20}$ arylalkyl group;

R₁ and R₂ are each independently selected from the group consisting of hydrogen, halogen, a cyano group, a hydroxyl group, a substituted or unsubstituted $C_1$~$C_{20}$ alkyl group, a substituted or unsubstituted $C_3$~$C_{20}$ cycloalkyl group, a substituted or unsubstituted $C_5$~$C_{20}$ heterocycloalkyl group, a substituted or unsubstituted $C_1$~$C_{20}$ alkoxy group, a substituted or unsubstituted $C_6$~$C_{20}$ aryl group, a substituted or unsubstituted $C_6$~$C_{20}$ arylalkyl group, and a substituted or unsubstituted $C_2$~$C_{20}$ heteroaryl group; and X is O, S, or NR' where R' is a substituted or unsubstituted $C_1$~$C_{20}$ alkyl group, a substituted or unsubstituted $C_3$~$C_{20}$ cycloalkyl group, a substituted or unsubstituted $C_1$~$C_{20}$ alkoxy group, a substituted or unsubstituted $C_6$~$C_{30}$ aryl group, or a substituted or unsubstituted $C_6$~$C_{30}$ aralkyl group.

2. The anthracene derivative compound of claim 1, which is a compound selected from compounds represented by Formulae 3 through 8 below:

Formula 3

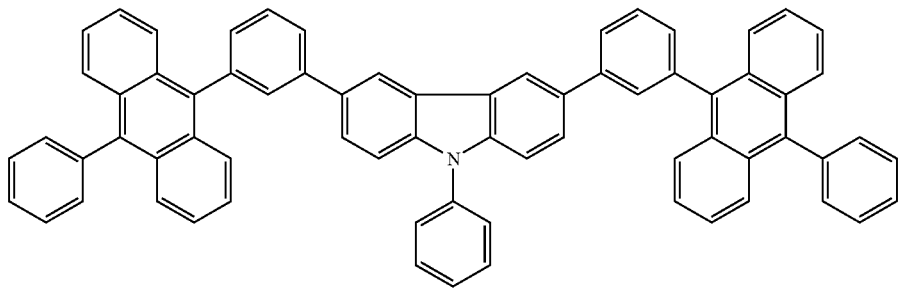

-continued

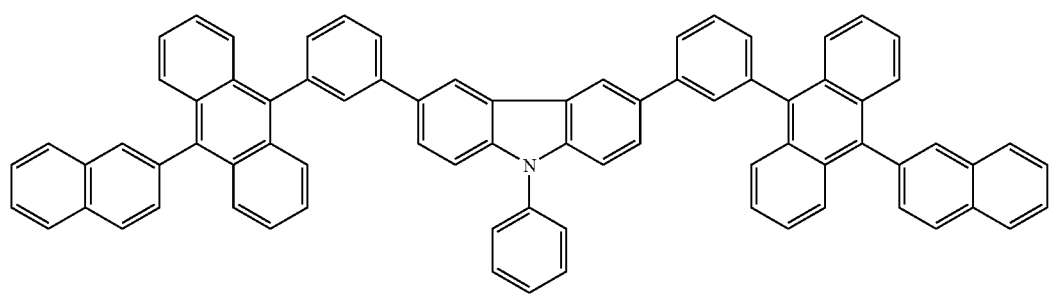

Formula 4

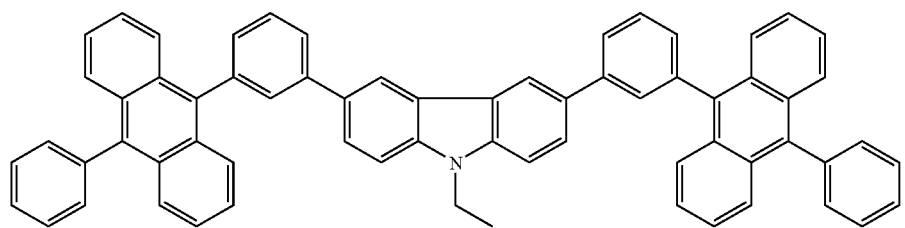

Formula 5

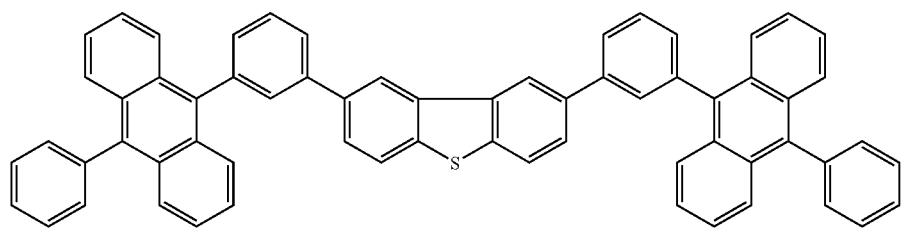

Formula 6

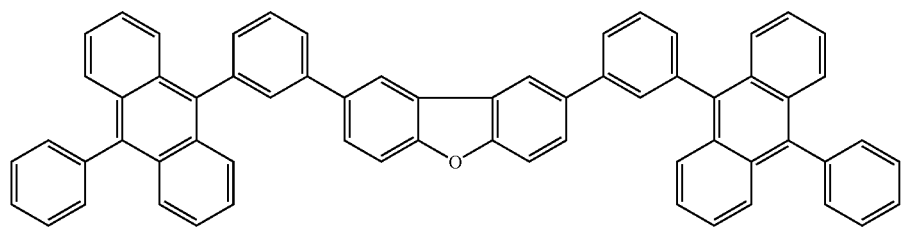

Formula 7

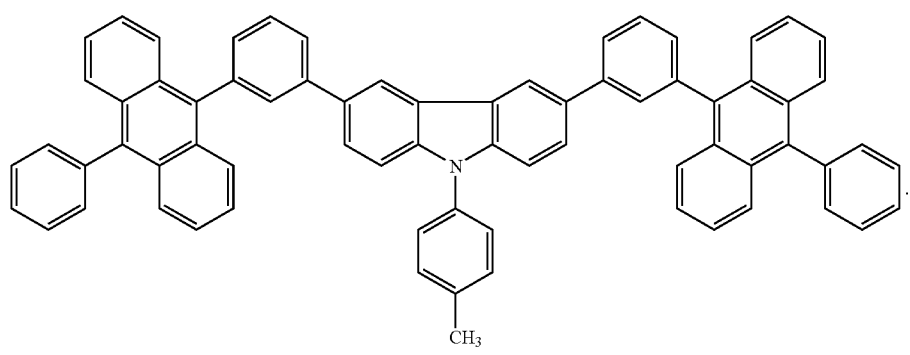

Formula 8

3. An organic light-emitting device comprising:
a first electrode;
a second electrode; and
at least one organic layer interposed between opposing surfaces of the first electrode and the second electrode, the organic layer comprising the compound of claim 1.

4. The organic light-emitting device of claim 3, wherein the organic layer is an emitting layer.

5. The organic light-emitting device of claim 3, further comprising at least one selected from the group consisting of a hole injection layer, a hole transport layer, an electron blocking layer, a hole blocking layer, an electron transport layer, and an electron injection layer, between the first electrode and the second electrode.

6. The organic light-emitting device of claim 5, which has a structure of first electrode/hole injection layer/emitting layer/electron transport layer/electron injection layer/second electrode, first electrode/hole injection layer/hole transport layer/emitting layer/electron transport layer/electron injection layer/second electrode, or first electrode/hole injection layer/hole transport layer/emitting layer/hole blocking layer/electron transport layer/electron injection layer/second electrode.

7. An organic light-emitting device comprising:
a first electrode;
a second electrode; and
at least one organic layer interposed between opposing surfaces of the first electrode and the second electrode, the organic layer comprising the compound of claim 1.

8. The organic light-emitting device of claim 7, wherein the organic layer is an emitting layer.

9. The organic light-emitting device of claim 7, further comprising at least one selected from the group consisting of a hole injection layer, a hole transport layer, an electron blocking layer, a hole blocking layer, an electron transport layer, and an electron injection layer, between the first electrode and the second electrode.

10. The organic light-emitting device of claim 7, which has a structure of first electrode/hole injection layer/emitting layer/electron transport layer/electron injection layer/second electrode, first electrode/hole injection layer/hole transport layer/emitting layer/electron transport layer/electron injection layer/second electrode, or first electrode/hole injection layer/hole transport layer/emitting layer/hole blocking layer/electron transport layer/electron injection layer/second electrode.

11. An organic light-emitting device comprising:
a first electrode;
a second electrode; and
at least one organic layer interposed between opposing surfaces of the first electrode and the second electrode, the organic layer comprising the compound of claim 2.

12. The organic light-emitting device of claim 11, wherein the organic layer is an emitting layer.

13. The organic light-emitting device of claim 11, further comprising at least one selected from the group consisting of a hole injection layer, a hole transport layer, an electron blocking layer, a hole blocking layer, an electron transport layer, and an electron injection layer, between the first electrode and the second electrode.

14. The organic light-emitting device of claim 11, which has a structure of first electrode/hole injection layer/emitting layer/electron transport layer/electron injection layer/second electrode, first electrode/hole injection layer/hole transport layer/emitting layer/electron transport layer/electron injection layer/second electrode, or first electrode/hole injection layer/hole transport layer/emitting layer/hole blocking layer/electron transport layer/electron injection layer/second electrode.

15. A method of manufacturing an organic light emitting device, comprising: forming a first electrode; forming an organic layer comprising an anthracene derivative compound according to claim 1 on a surface of the first electrode; and forming a second electrode on a surface of the organic layer opposite the first electrode.

16. An organic light emitting device prepared according to the method of claim 15.

* * * * *